United States Patent [19]

Shoesmith

[11] Patent Number: Plant 5,285

[45] Date of Patent: Sep. 18, 1984

[54] CHRYSANTHEMUM PLANT NAMED MERRIMENT

[75] Inventor: Leonard H. Shoesmith, Surrey, England

[73] Assignee: Pan American Plant Company, Parrish, Fla.

[21] Appl. No.: 406,100

[22] Filed: Aug. 6, 1982

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Merriment and particularly characterized by its flat capitulum form and single capitulum type, yellow ray floret color, 50–70 mm. diameter across the face of the capitulum, 90–135 mm. length peduncles, uniform nine week response, 1.5 to 2 meter length with no long days, and by its semiupright branching habit.

2 Drawing Figures

The present invention comprises a new and distinct cultivar of *Chrysanthemum morifolium,* Ramat., hereinafter referred to by the cultivar name Merriment.

Merriment is a product of a planned breeding program which had the objective of creating new chrysanthemum cultivars with single capitulum type, yellow ray floret color, 8 to 9 week flowering response, and having the ability to produce commercially acceptable quality in a year round pompom chrysanthemum program. Such traits in combination were not present in previously available commercial cultivars.

Merriment was originated from a hybridization made in a controlled breeding program in Westfield, Woking, England in 1976. The male and female parents are unknown at this time.

Merriment was discovered and selected as one flowering plant within the progeny of the parentage by Leonard H. Shoesmith on November, 1977 in a controlled environment in West Chicago, Ill., and given code number Sp6-270-Y. The first act of asexual reproduction of Merriment was accomplished when vegetative cuttings were taken from the initial selection in February, 1978, in a controlled environment in West Chicago, Ill. by a technician working under formulations established and supervised by Leonard H. Shoesmith. Horticultural examination of selected units initiated in March, 1978 has demonstrated that the combination of characteristics as herein disclosed for Merriment are firmly fixed and are retained through successive generations of asexual reproduction.

Merriment has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteritics of Merriment which in combination distinguish this chrysanthemum as a new and distinct cultivar:

1. Flat capitulum form.
2. Single capitulum type.
3. Yellow ray floret color.

4. Diameter across the face of the capitulum 50–70 mm.
5. Long peduncles, 90–135 mm. in length.
6. Uniform 8–9 week photoperiodic flowering response to short days.
7. Height 1.5 to 2 m with no long days.
8. Semi-upright branching habit.

Of the many commercial cultivars known to the present inventor, the most similar in comparison to Merriment is Florida Marble, disclosed in U.S. Plant Pat. No. 3,288. In comparison to Florida Marble, Merriment is 7 to 10 days earlier in response, has a brighter yellow flower, and less compounding of spray form. The capitulum form and capitulum type are similar to those same characteristics of Florida Marble.

The accompanying photographic drawings show typical inflorescence and foliage characteristics of Merriment, with colors being as nearly true as possible with illustrations of this type. Sheet 1 is a color photograph in perspective of Merriment. Sheet 2 is a black and white photoprint of the underside of typical foliage of Merriment at various stages of growth or positioning on the plant.

In the following description color references are made to The Royal Horticultural Society Colour Chart. The color values were determined between 3:30–4:30 P.M. on May 24, 1982 under 3200K–500W intensity incandescent light at Bradenton, Fla.

CLASSIFICATION

Botanical: *Chrysanthemum morifolium,* Ramat., cv Merriment.

Commercial: Cut decorative spray or pompom.

INFLORESCENCE

Capitulum:

*Form.*—Flat.

*Type.*—Single.

*Diameter across face.*—50–70 mm.

Corolla of ray florets:

*Color (general tonality from a distance of* 1.5 meters)-.—Bright clear yellow.

*Color (abaxial).*—9C.

*Color (adaxial).*—9A–9B.

Corolla of disc florets:

*Color* (*mature*).—Yellow.

*Color* (*immature*).—Lime green.

Reproductive organs:

*Androecium.*—Present disc florets only; numerous.

*Gynoecium.*—Present ray florets only; one per floret.

PLANT

General appearance:

*Height.*—1.5–2 Meters high given no long days, year round.

Foliage:

*Color* (*abaxial*).—138C.

*Color* (*adaxial*).—138A.

*Shape.*—Deeply lobed and slightly serrated.

I claim:

1. A new and distinct chrysanthemum cultivar named Merriment, as described and illustrated, and particularly characterized by its flat capitulum form and single capitulum type, yellow ray floret color, 50–70 mm. diameter across the face of the capitulum, 90–135 mm. length peduncles, uniform nine week response, 1.5 to 2 meter length with no long days, and by its semiupright branching habit.

* * * * *

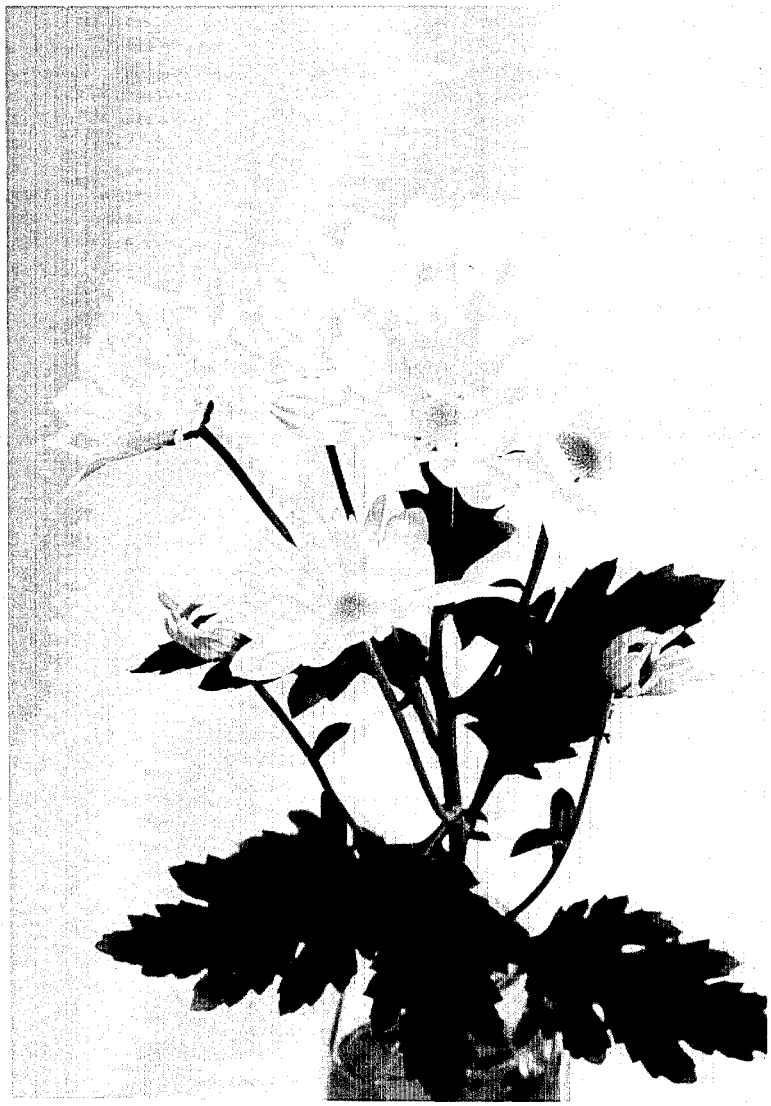

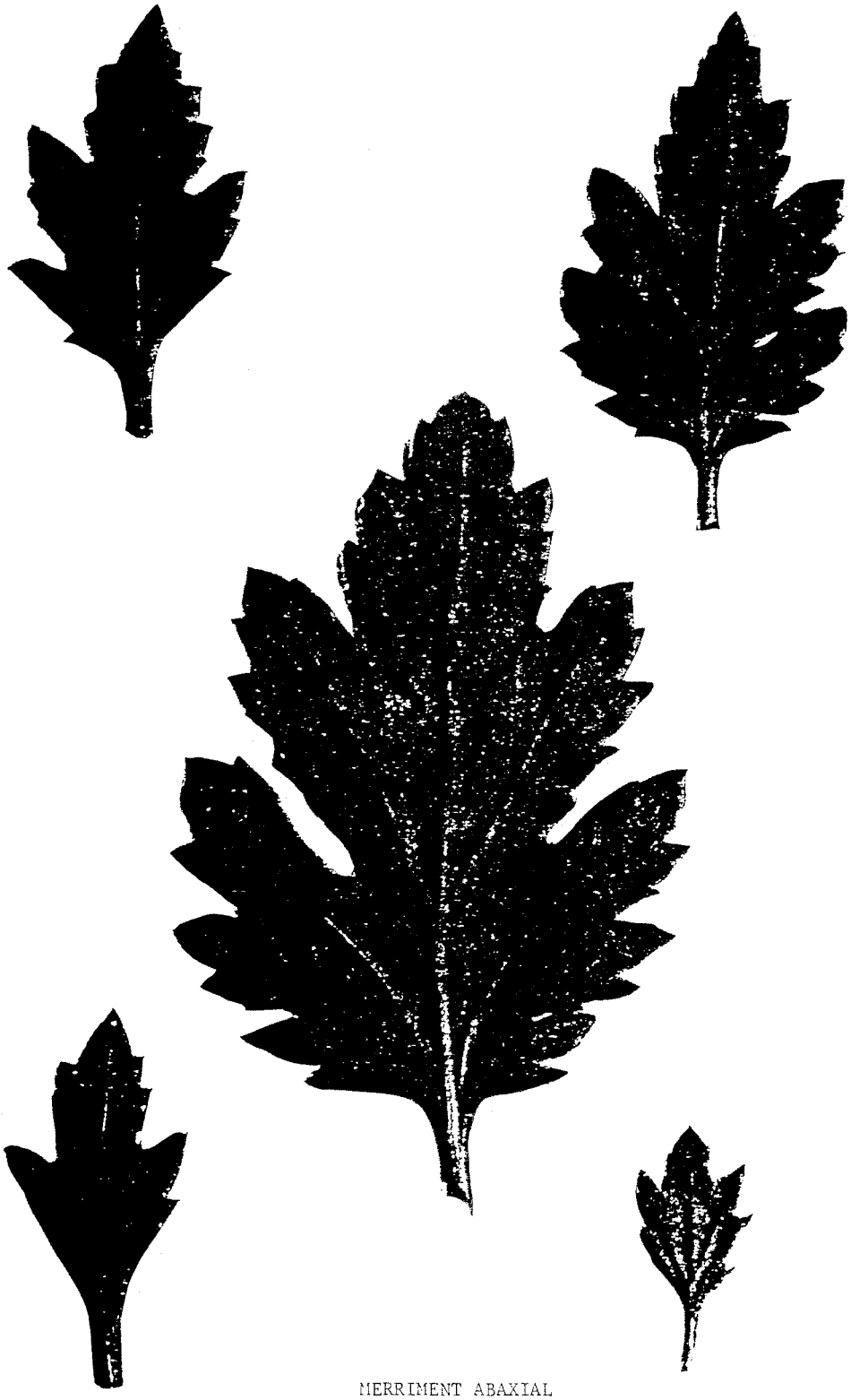
MERRIMENT ABAXIAL